United States Patent [19]

Allen et al.

[11] Patent Number: 5,021,551

[45] Date of Patent: Jun. 4, 1991

[54] METHOD OF ENHANCING PEPTIDE IMMUNOGENICITY

[75] Inventors: Paul M. Allen; Emil R. Unanue, both of St Louis, Mo.

[73] Assignee: Washington University, St. Louis, Mo.

[21] Appl. No.: 298,377

[22] Filed: Jan. 18, 1989

[51] Int. Cl.[5] .......................... A61K 37/02; C07K 1/00
[52] U.S. Cl. .................................... 530/345; 530/359; 530/806; 530/853
[58] Field of Search ............... 530/359, 806, 853, 345; 514/2, 15, 14, 16

[56] References Cited

PUBLICATIONS

R. B. Merrifield, "Angewandte Chemie", vol. 97 (1985), p. 801–812.
Morrison and Boyd, 3rd Ed., "Organic Chemistry", Allyn and Bacon (1979) p. 603.
James T. Barrett, "Textbook of Immunology", C. V. Mosby Co. (1978) 3rd Ed. pp. 70–79.

*Primary Examiner*—John Doll
*Assistant Examiner*—Rennett M. Celsa
*Attorney, Agent, or Firm*—Scott J. Meyer; James W. Williams, Jr.

[57] ABSTRACT

A method is disclosed for enhancement of the immunogenicity of a T cell immunogenic peptide which comprises adding an acidic amino acid at the N-terminus and/or a positive charge at the C-terminus of said peptide.

8 Claims, 3 Drawing Sheets

METHOD OF ENHANCING PEPTIDE IMMUNOGENICITY

BACKGROUND OF THE INVENTION

This invention relates to a method of enhancing the immunogenicity of T cell immunogenic peptides.

Only recently has the basis of recognition of protein antigens by helper T cells (Th) been defined in molecular terms. Th cells (i.e., CD4 positive) recognize a fragment or processed form of a foreign antigen bound to a class II major histocompatibility molecule (i.e., Ia) on the surface of an antigen presenting cell. See Unanue and Allen, *Science* 236, 551–557(1987), for a recent review.

Many different determinants of peptide antigens have been identified and characterized but the precise conformation of any of these peptides as they are bound to Ia and recognized by the T cell receptor is not known; proposed conformations have been made ranging from an alpha-helix to a beta-pleated sheet. For several years a group led by the present inventors has studied the immunogenic properties of a determinant of hen egg-white lysozyme (HEL) contained in the tryptic fragment encompassing residues 46-61. See Allen and Unanue, *J. Immunol.* 132, 1077 (1984); Allen et al., *Proc. Natl. Acad. Sci.* USA 81, 2489 (1984); Babbitt et al., *Nature* 317, 359 (1985); and Babbitt et al., *Proc. Natl. Acad. Sci.* USA 83, 4509–4513 (1986). The analysis revealed that the 10 amino acid peptide, HEL(52-61), was the smallest stimulatory peptide. Through the use of a series of substituted peptides, potential roles were assigned to each of the 10 amino acid residues in HEL(52-61) by Allen et al., *Nature* 327, 713-715 (1987). It was proposed that residues 53, 56, and 57 contacted the T cell receptor, residues 52, 58, and 61 contacted the Ia molecule, while residues 54, 55, 59, and 60 were spacer residues. When this peptide was modeled into an alpha-helix, a spatial segregation of the T cell contact residues from the Ia contact residues was observed. From this result it was proposed that HEL(52-61) was assuming an alpha-helical conformation as it bound to I-A$^k$ and as such was recognized by the appropriate T cell receptor.

BRIEF DESCRIPTION OF THE INVENTION

In accordance with the present inventions a method is provided for the enhancement of the immunogenicity of T cell immunogenic peptides. The method comprises adding an acidic amino acid at the amino terminus or a positive charge at the carboxy terminus, or by incorporating both said additions to the peptide. Changing the C-terminus from an acid to an amide changes its nature from hydrophilic to hydrophobic. Similarly, the addition of a second residue at the amino terminus may foster ionic interactions. These changes to the peptide also tend to stabilize its helical conformation.

The method of the invention is illustrated in a preferred embodiment by adding the acidic residue, Glu, to the N-terminus and/or changing the C-terminus to amide instead of a free acid to eliminate a negative charge from the C-terminus of the peptide. In the case of the specific illustrative immunogenic peptide HEL(52-61), the method can be shown by the following structural changes to the peptide:

Normal HEL(52-61)
Asp—Tyr—Gly—Ile—Leu—Gln—Ile—Asn—Ser—Arg

-continued

Modified HEL(52-61) or $^-$52-61$^+$
Glu—Asp—Tyr—Gly—Ile—Leu—Gln—Ile—Asn—Ser—ArgNH$_2$ This modified HEL(52-61) is also conveniently referred to herein as peptide $^-$52-61$^+$ in which the minus and plus signs indicate the position of the charges in the molecule. It was tested for its ability to stimulate two HEL(52-61) specific T cell hybridomas, namely 2A11 and 3A9 [Allen and Unanue, *J. Immunol.* 132, 1077 (1984); Allen et al., *Proc. Natl. Acad. Sci.* USA 81, 2489 (1984)]. Comparisons were made with the normal peptide HEL(51-61) which is the same length as $^-$52-+61. HEL(51-61) has a N-terminal Thr. In these tests, peptide $^-$52-61$^+$ was much more stimulatory than the HEL(51-61) peptide, being about 300 fold more potent in stimulating the 3A9 T cell and about 100 fold more potent for the 2A11 T cell.

The $^-$52-61$^+$ peptide contained two substitutions, one to each of the termini. Modified HEL(52-61) peptides containing only the individual substitutions (namely peptides $^-$52-61 and 52-61$^+$) were also tested for stimulatory ability. It was found that both of the single modifications found in $^-$52-61$^+$ enhanced the responses in both T cell hybridomas 2A11 and 3A9, but the conversion to a C-terminal amide had a more pronounced effect than the addition of the Glu residue at the N-terminal.

The modified peptide $^-$52-61$^+$ also showed enhancement of in vivo priming ability in which mice were immunized with peptide and 7 days later the popliteal lymph node cells were tested in an in vitro proliferation assay.

The method of the invention thus is useful for preparing better immunogens for prophylactic immunization, especially relatively short T cell immunogenic peptides of about 10–20 amino acids.

DETAILED DESCRIPTION OF THE INVENTION

Figure 1A:
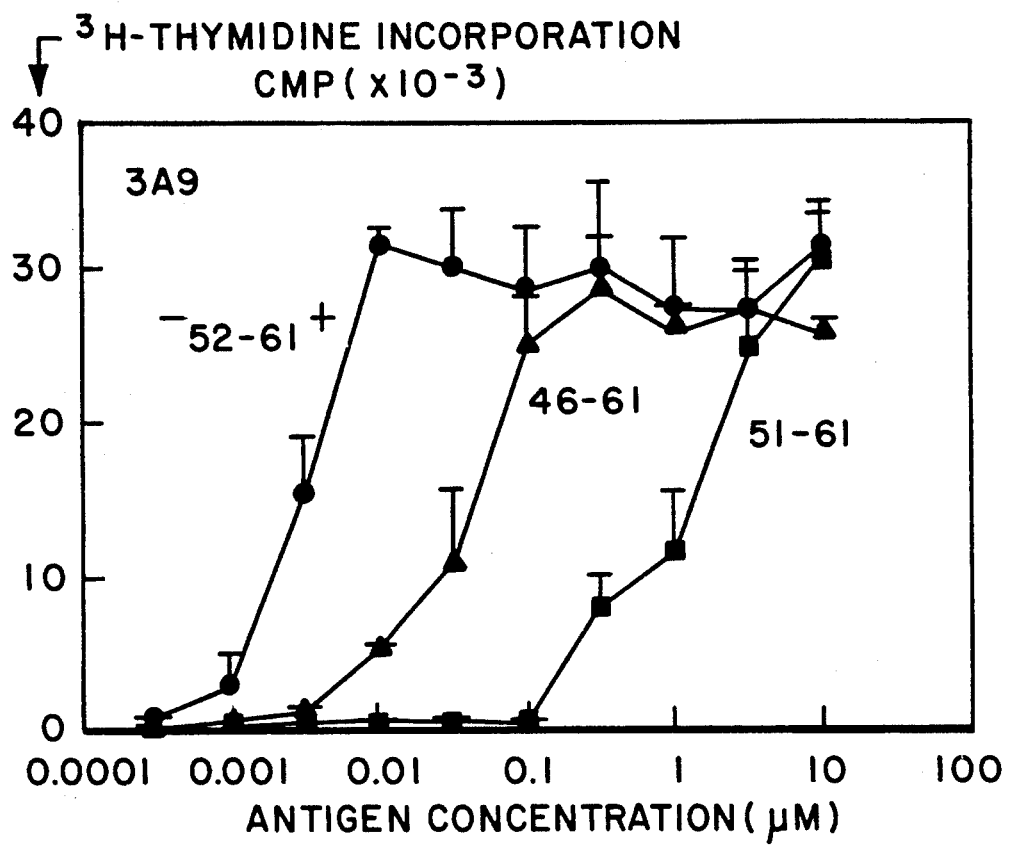
Figure 1B:
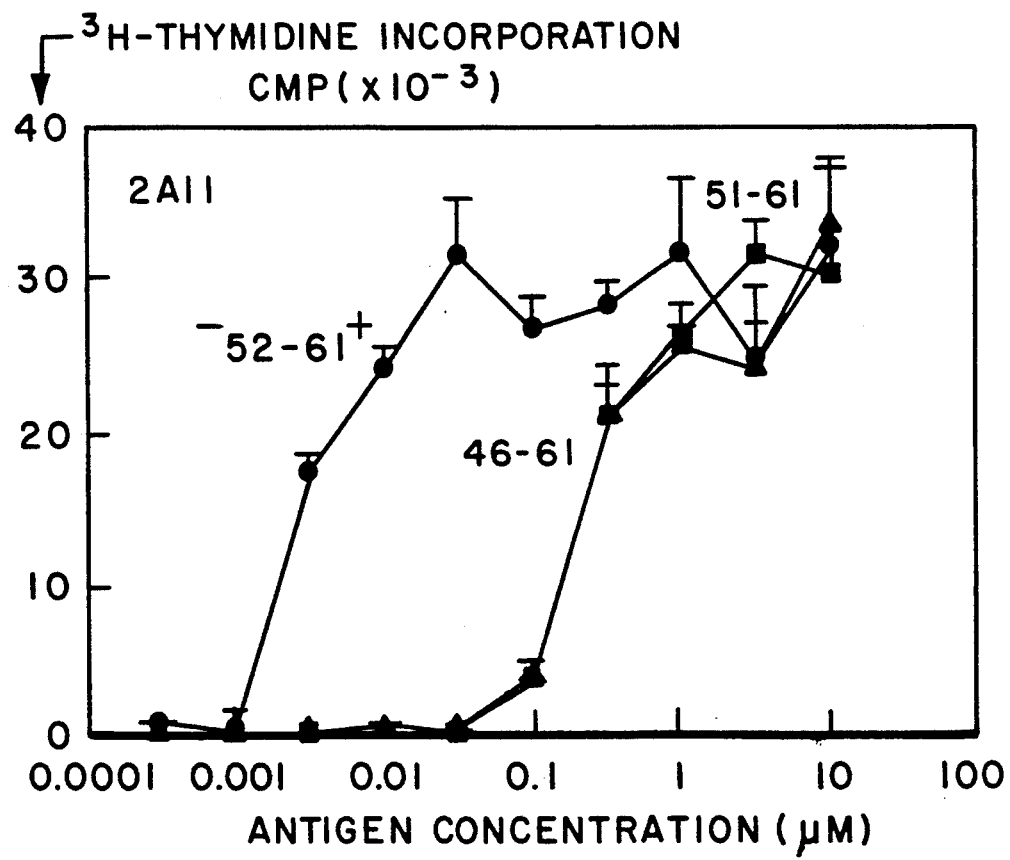

While the specification concludes with claims particularly pointing out and distinctly claiming the subject matter regarded as forming the present invention, it is believed that the invention will be better understood from the following detailed description of illustrative embodiments of the invention in conjunction with the appended drawings in which:

FIG. 1a and 1b are graphical representations which show the response of monoclonal antibodies 3A9 (FIG. 1a) and 2A11 (FIG. 1b) to a modified T cell immunogenic peptide $^-$52-61$^+$(●) in one embodiment of the invention compared to normal, peptides HEL (46-61) (▲), and HEL (51-61) (■). The level of T cell stimulation was determined by quantitating the amount of IL-2 released. The assay was performed as described hereinafter in Materials and Methods of the Examples. The sequence of the peptides are given in Table 1, below. The values represent the mean ± standard deviation of triplicate values.

Figure 2A:
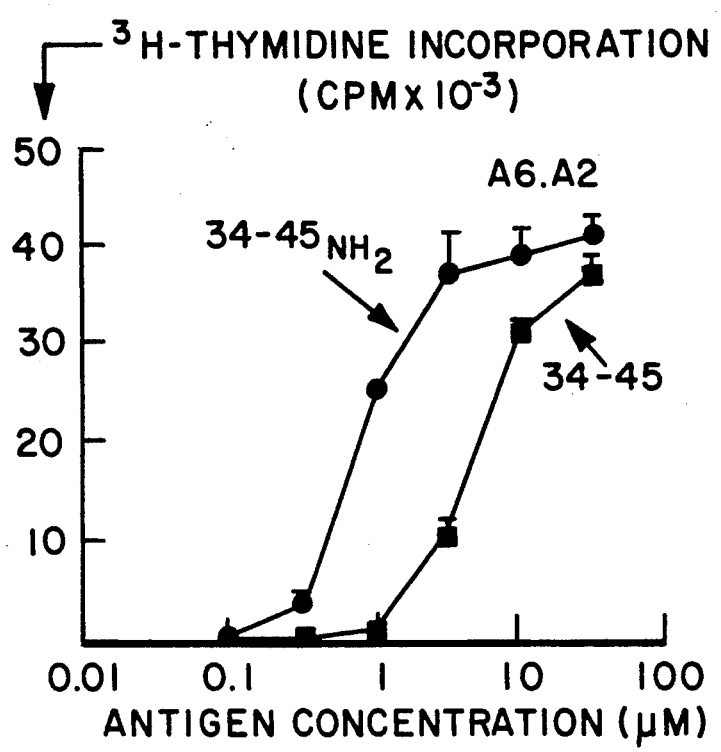
Figure 2B:
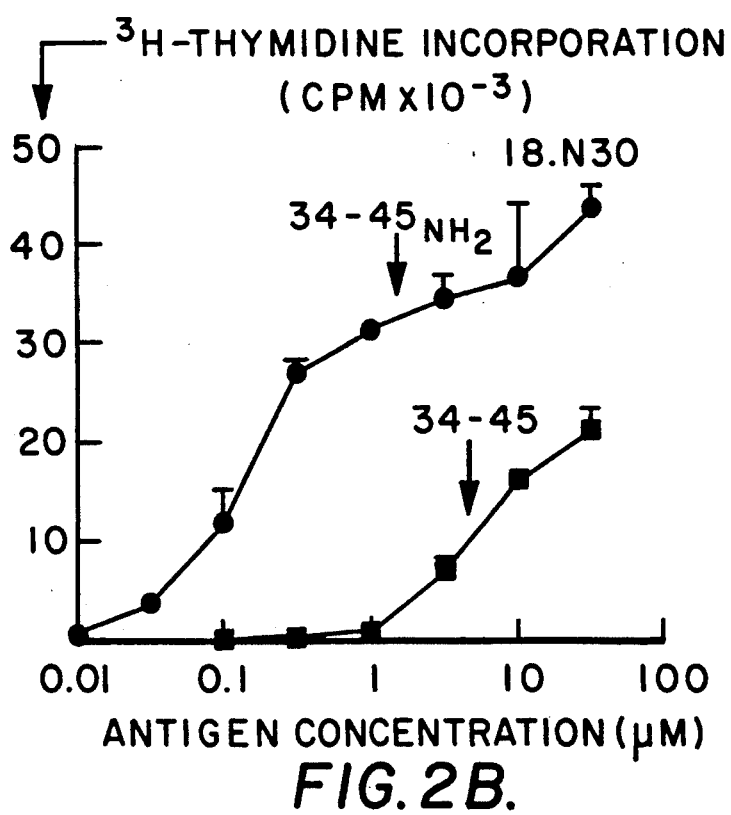

FIG. 2a and 2b are graphical representation which show the stimulation of two T cell hybridomas, A6.A2 (FIG. 1a) and 18N.30 (FIG. 1b), that react with a modified T cell immunogenic peptide 34-45$_{NH_2}$ (●) in another embodiment of the invention compared to normal peptide HEL (34-45) (■). The assay was performed as described hereinafter in Materials and Methods of the Examples except fixed TA3 cells were used as the source of antigen-presenting cell. The sequence of the peptides are given in Table 3, below.

Figure 3:
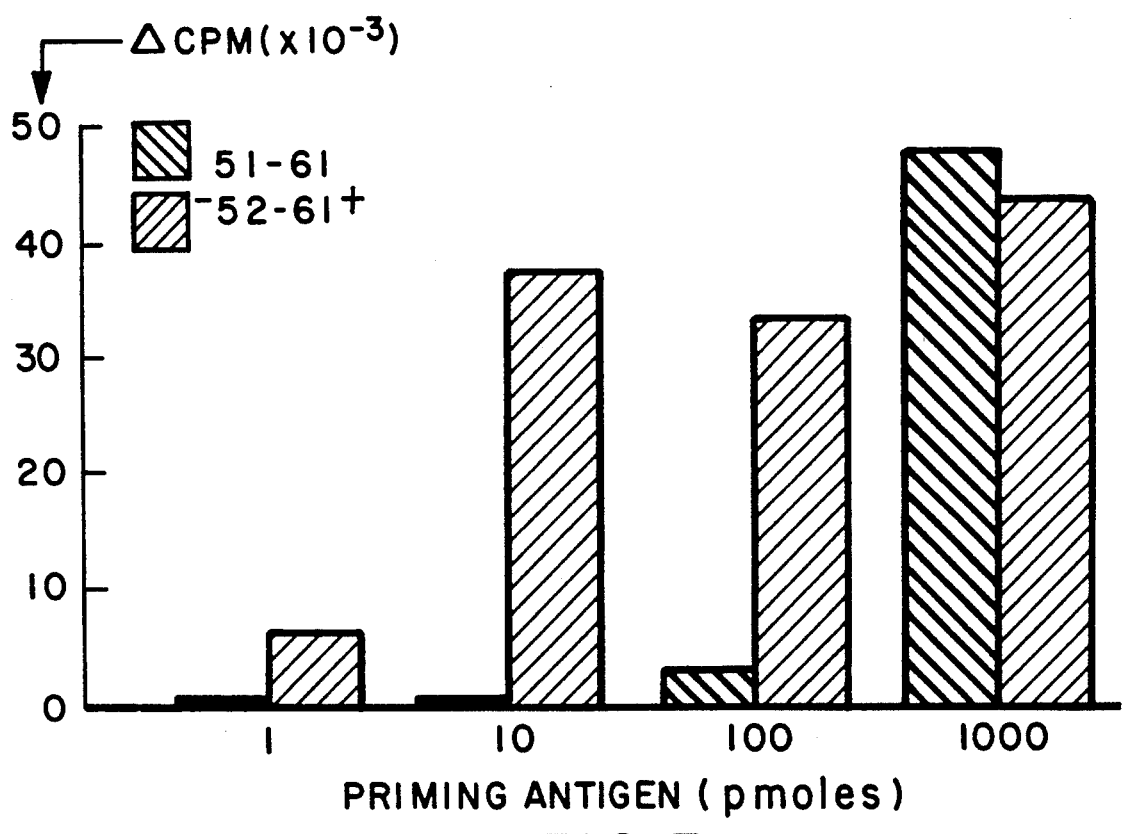

FIG. 3 is a graphical representation which shows a comparision of peptide HEL (51-61) and the modified immunogenic peptide −52-61+of FIG. 1 for in vivo priming ability.

In order to illustrate the invention in detail, the following laboratory preparative work was carried out by way of exemplification although it will be understood that the invention is not limited to these specific examples.

EXAMPLES

Materials and Methods

T Cell Stimulation Assay

The level of T cell stimulation was determined as previously described in detail by Allen and Unanue, *J. Immunol.* 132, 1077 (1984). In general, the level of T cell stimulation was determined by quantitating the amount of IL-2 produced by the T cell hybridomas. IL-2 was bioassayed by determining the level of $^3$H-Thymidine incorporation of the IL-2 dependent cell line, CTLL, 24 hours after culture in the test culture media. The source of antigen presenting cells were either peptone elicited peritoneal macrophages from CBA/J mice previously infected with *Listeria monocytogenes* or the B cell hybridoma, TA3 [Allen and Unanue, Id.; Allen et al, *Proc. Natl. Acad. Sci. USA* 81, 2489 (1984)]. Both sources of antigen presenting cells were fixed with paraformaldehyde prior to exposure to antigen.

Peptide Synthesis

Most of the peptides used in these examples were synthesized by the standard t-Boc methodology using a BioSearch XXXX or an ABI XXXX synthesizer. Some peptides were synthesized using the FMOC procedure on a RaMPS synthesizer. All of the peptides were purified by HPLC and analyzed by amino acid composition. When necessary, the peptides were further analyzed by amino acid sequence or by FAB-MS spectrometry.

In order to further illustrate the invention, a unique derivative of the known T cell immunogenic peptide, HEL(52-61), was prepared. HEL(52-61) possesses two charged residues, an Asp at position 52 and an Arg at position 61 (see Table 1, below). The new peptide, −52-61+, was synthesized to contain a C-terminal amide instead of a free acid to eliminate a negative charge from the C-terminus. A second change was the addition of a second acidic residue, a Glu, to the N-terminus (Table 1).

Peptide −52-61+was tested for its ability to stimulate two HEL (52-61) specific T cell hybridomas, 2AII and 3A9. As shown in FIG. 1, −52-61+was much more stimulatory than the 51-61 peptide, being about 300 fold more potent in stimulating the 3A9 T cell and about 100 fold more potent for the 2All T cell. The peptide 51-61 was used for comparison since it has the same length as −52-61+. However, peptide 51-61 was also more stimulatory than HEL (46-61). Thus by making substitutions consistent with the stabilization of a helix dipole, a much more stimulatory peptide was generated.

The −52-61+. peptide contained two substitutions, one to each of the termini. To ascertain the relative contribution of each of them to this increase in immunogenicity, a set of peptides was generated that contained the individual substitutions as well as other related modifications. These peptides were then tested for their stimulatory ability (see Table 2). Both of the single modifications found in −52-61+. enhanced the responses to both T cell hybridomas 2All and 3A9, but the conversion to a C terminal amide had a more pronounced effect than the addition of the Glu residue at the amino terminus. Thus each charge in −52-61+. contributed to the observed ± enhancement, with the C terminal amide having more of an effect.

For further tests, a peptide was prepared to contain opposite charged residues located next to the terminal residues, designated +−52-61−+(Table 1). As shown in Table 2, its activity was drastically reduced compared to that of −52-61+. For 3A9 cells it was less active than HEL (52-61), while for 2A11 it only was slightly more stimulatory. Peptides were also synthesized with multiple charged residues at each of the termini in order to further enhance their activity. These included the addition of 3 or 6 Glu residues on the N terminus, or 3 Arg residues on the C terminus. All of these peptides had the same enhanced activity as the −52-61+, but no additional enhancement was observed (data not shown).

It was also determined whether the changes that enhanced the immunogenicity of HEL (52-61) could be extrapolated to another peptide of HEL which had been previously studied, namely the peptide comprising residues 34-45 [Allen et al, *Immun. Rev.* 98, 171 (1987)]. This peptide contained a charge distribution similar to that observed with HEL (52-61), with a Glu residue positioned near the N terminus and a C terminal Arg (Table 3). The peptide HEL (34-45) was synthesized with a C terminal amide and its ability to stimulate two HEL (34-45) specific hybridomas was tested (FIG. 2). Both hybridomas responded better to HEL (34-45) with a C terminal amide compared to the unmodified HEL (34-45). However, these increases differed between the two cell lines, being 50 fold for A6.A2 and 250 fold for 18N.30. A peptide that contained a C terminal amide as well as a Phe to Glu replacement at position 34 in an analogous manner to −52-61+. was also tested. This peptide behaved identically to that which only contained the C terminal amide. This result is consistent with that observed with HEL (52-61) in that it appeared that the C terminal amide was mostly responsible for the observed enhancement.

Enhancement of in vivo priming ability

To determine if a similar change in immunogenicity was observed in vivo, CBA/J mice were immunized with various doses of either 51-61 or −52-61+, and 7 days later the popliteal lymph node cells were tested in an in vitro proliferation assay. FIG. 3 shows that −52-61+. was approximately 1000 times better at immunizing than 51-61. A detectable response was observed with −52-61+ when priming at 1 pmole whereas with 51-61 a slight response was observed at 100 pmole, and not until priming at 1000 pmole was a good response observed. Thus this same enhancement of 52-61 that was observed in vitro was also evident in vivo when bulk populations of T cells were examined.

TABLE 1

| Peptide Designation | Sequence |
|---|---|
| | 46 _ 52 61 |
| 46-61 | +N T D G S T D Y G I L Q I N S R− |

TABLE 1-continued

| Peptide Designation | Sequence |
|---|---|
| 52-61 | +D Y G I L Q I N S R⁺− |
| 51-61 | +T⁻ D Y G I L Q I N S R− |
| 52-61+ | +E⁻ D⁻ Y G I L Q I N S R⁺ |
| 52-61⁺ | +D⁻ Y G I L Q I N S R⁺ |
| ⁻52-61 | +E⁻ D⁻ Y G I L Q I N S R⁺− |
| ⁺⁻52-61⁻⁺ | +K⁺⁻ D Y G I L Q I N S R⁺⁻ E− |

The amino acid sequence of HEL (46-61) and derivatives are shown. The standard one letter codes are used for the amino acids. The "−" and "+" signs reflect the position of the charges in the peptide. The symbols above the line represent the charge of the amino acid side chains at pH 7, while the symbols on the line represent the charge of the termini. A "−" on the C terminus represents a COOH group, while no symbol represents a CONH$_2$ group.

TABLE 2

| Peptide | Relative Stimulatory Capacity T Cell | |
|---|---|---|
| | 3A9 | 2A11 |
| 52-61 | 1 | 1 |
| ⁻52-61⁺ | 300 | 100 |
| ⁻52-61 | 30 | 3 |
| 52-61⁺ | 100 | 100 |
| ⁺⁻52-61⁻⁺ | 0.3 | 10 |

The relative stimulatory capacity of derivatives of HEL (52-61) are shown. The sequences of the peptides are given in Table 1. The relative stimulatory capacity of a peptide was determined by the relative shift in the concentration of antigen required for a 50% maximal response. For example, 300 fold less ⁻52-61⁺. was required for a 50% maximal response than 52-61 with 3A9 T cells. The stimulation of 3A9 and 2A11, two HEL (46-61) specific T cells, was determined as described in Materials and Methods. This test was performed three times, with identical results. A representative test is shown.

TABLE 3

| Peptide Designation | 34 | 45 |
|---|---|---|
| 34-45 | +F E⁻ S N F N T Q A T N⁻ R− |
| 34-45$_{NH2}$ | +F E⁻ S N F N T Q A T N⁻ R |

The sequence of HEL (34-45) is shown using the standard single letter codes for amino acids. The charges are the same as described for Table 1, except the C terminal amide (CONH$_2$) is represented as NH$_2$.

Amino acids are shown herein either by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such further examples be included within the scope of the appended claims.

What is claimed is:

1. A method of enhancing the immunogenicity of a T cell immunogenic peptide which binds to Ia molecules comprising carrying out a reaction of covalently bonding an acidic amino acid to the peptide amino terminus or changing the free acid of the peptide carboxy terminus to amide or by carrying out both said reactions of the peptide.

2. The method of claim 1 in which an acidic amino acid is covently bonded to the amino-terminus of the peptide.

3. A method of claim 2 in which the acidic amino acid is Glu.

4. A method of claim 1 in which a positive charge is covently bonded to the carboxy-terminus of the peptide.

5. A method of claim 4 in which the carboxy-terminus is changed from free acid to amide.

6. A method of claim 1 in which the amino acid Glu is covently bonded to the amino-terminus and the carboxy C-terminus is changed from free acid to amide.

7. The method of claim 1 in which the T cell immunogenic peptide is derived from hen egg white lysozyme.

8. The method of claim 1 in which the T cell immunogenic peptide is HEL(52-61) or HEL(34-45).

* * * * *

UNITED STATES PATENT AND TRADEMARK OFFICE
CERTIFICATE OF CORRECTION

PATENT NO. : 5,021,551

DATED : June 4, 1991

INVENTOR(S) : Paul M. Allen and Emil R. Unanue

It is certified that error appears in the above-identified patent and that said Letters Patent is hereby corrected as shown below.

Col. 1, line 47, "inventions" should read --invention--;
Col. 6:
Claim 2, line 40, "covently" should read --covalently--;
Claim 4, line 45, "covently" should read --covalently--;
Claim 6, line 40, "covently" should read --covalently.

Signed and Sealed this

Second Day of February, 1993

Attest:

STEPHEN G. KUNIN

*Attesting Officer*  *Acting Commissioner of Patents and Trademarks*